US012478472B2

(12) United States Patent
Casley et al.

(10) Patent No.: US 12,478,472 B2
(45) Date of Patent: Nov. 25, 2025

(54) DELIVERY SYSTEM WITH PACING ELEMENT

(71) Applicant: Medtronic Vascular Galway, Galway (IE)

(72) Inventors: Mark Casley, Santa Rosa, CA (US); Declan Costello, Co. Mayo (IE)

(73) Assignee: Medtronic Vascular Galway, Galway (IE)

( * ) Notice: Subject to any disclaimer, the term of this patent is extended or adjusted under 35 U.S.C. 154(b) by 0 days.

(21) Appl. No.: 18/444,721

(22) Filed: Feb. 18, 2024

(65) Prior Publication Data

US 2024/0335285 A1 Oct. 10, 2024

Related U.S. Application Data

(60) Continuation of application No. 17/561,773, filed on Dec. 24, 2021, now abandoned, which is a continuation of application No. 16/567,658, filed on Sep. 11, 2019, now Pat. No. 11,241,311, which is a division of application No. 15/131,137, filed on Apr. 18, 2016, now Pat. No. 10,426,615, which is a continuation of application No. 13/916,858, filed on Jun. 13, 2013, now Pat. No. 9,326,854.

(51) Int. Cl.

| | |
|---|---|
| ***A61F 2/24*** | (2006.01) |
| ***A61N 1/05*** | (2006.01) |
| ***A61N 1/372*** | (2006.01) |
| ***A61N 1/375*** | (2006.01) |

(52) U.S. Cl.
CPC .......... *A61F 2/2436* (2013.01); *A61F 2/2418* (2013.01); *A61N 1/0573* (2013.01); *A61N 1/37205* (2013.01); *A61N 1/3756* (2013.01); *A61F 2250/0001* (2013.01); *A61F 2250/0043* (2013.01)

(58) Field of Classification Search
CPC ........ A61F 2/24; A61F 2/2427; A61F 2/2436; A61F 2/2466; A61N 1/05; A61N 1/056; A61N 1/36; A61N 1/362
See application file for complete search history.

(56) References Cited

U.S. PATENT DOCUMENTS

| | | | |
|---|---|---|---|
| 5,250,071 | A | 10/1993 | Palermo |
| 5,487,760 | A | 1/1996 | Villafana |
| 7,643,879 | B2 | 1/2010 | Shuros et al. |

(Continued)

FOREIGN PATENT DOCUMENTS

| | | |
|---|---|---|
| WO | 2008/027261 | 3/2008 |

*Primary Examiner* — Todd J Scherbel
(74) *Attorney, Agent, or Firm* — Medler Ferro Woodhouse & Mills PLLC

(57) ABSTRACT

Medical device delivery assemblies are disclosed. The assembly may include a catheter-based delivery system. The assembly may include a pacing element to pace a patient's heart before, during, or after a procedure. The pacing element may be a detachable, implanting pacing element. The pacing element may be an implantable pacemaker and the implantable pacemaker may be disposed on a catheter-based delivery system. The assembly may include a prosthetic heart valve with one or more pacing elements on it. The pacing element may include a pacing strip or strips. These strips may be conductive or insulative. These strips may prevent, treat, or correct abnormal electrical communication in a heart.

6 Claims, 9 Drawing Sheets

(56) References Cited

U.S. PATENT DOCUMENTS

| | | | |
|---|---|---|---|
| 9,326,854 | B2 | 5/2016 | Casley et al. |
| 10,426,615 | B2 | 10/2019 | Casley et al. |
| 2007/0142907 | A1 | 6/2007 | Moaddeb et al. |
| 2008/0021505 | A1 | 1/2008 | Hastings et al. |
| 2008/0051838 | A1 | 2/2008 | Shuros et al. |
| 2009/0299420 | A1 | 12/2009 | Shuros et al. |
| 2009/0318984 | A1 | 12/2009 | Mokelke et al. |
| 2010/0049306 | A1 | 2/2010 | House et al. |
| 2010/0198346 | A1 | 8/2010 | Keogh et al. |
| 2012/0022633 | A1 | 1/2012 | Olson et al. |
| 2012/0172690 | A1 | 7/2012 | Anderson et al. |
| 2012/0215299 | A1 | 8/2012 | Melzer et al. |
| 2013/0035748 | A1 | 2/2013 | Bonner et al. |
| 2013/0079798 | A1 | 3/2013 | Tran et al. |
| 2013/0178908 | A1 | 7/2013 | Huber |
| 2014/0073978 | A1 | 3/2014 | Shuros et al. |

DELIVERY SYSTEM WITH PACING ELEMENT

CROSS-REFERENCE TO RELATED APPLICATIONS

This application is a continuation of U.S. patent application Ser. No. 17/561,773, filed Dec. 24, 2021, which is a continuation of U.S. patent application Ser. No. 16/567,658, filed Sep. 11, 2019, now U.S. Pat. No. 11,241,311, which is a division of U.S. patent application Ser. No. 15/131,137, filed Apr. 18, 2016, now U.S. Pat. No. 10,426,625, which is a continuation of U.S. patent application Ser. No. 13/916,858, filed Jun. 13, 2013, now U.S. Pat. No. 9,326,854, the disclosures of which are incorporated herein by reference in their entirety.

BACKGROUND

Often patients have a problem with their heart beating at a regular and appropriate pace. Many patients require a pacemaker or similar device to aid in pacing their heart. Further, certain patients require heart valve repair or a prosthetic heart valve implant to help with related or separate problems from these pacing issues. During medical procedures, such as a trans-catheter aortic valve implant (TAVI) procedure, physicians may want to pace the heart. In other instances physicians may desire to pace the patient's heart following these or other procedures.

In some instances pacing of a patient's heart may be required after a previous procedure, such as implanting a prosthetic heart valve. Thus there is a need to help with pacing of the heart during such repair or implant procedures as well as after such procedures. There is a need to eliminate multiple procedures and to simplify the process. There is a need for a delivery system or apparatus for delivering a biocompatible material and to prevent or correct pacing problems.

BRIEF SUMMARY

In accordance with some embodiments, a delivery system comprises a pacing element. This pacing element may be disposed on the tip of the delivery system. This pacing element may also be disposed on a portion of a prosthesis, such as a prosthetic heart valve. This pacing element may be included on a portion of the frame as a strip or a coating of highly conductive material. This pacing element may comprise an implantable pacemaker. This implantable pacemaker may be disposed on a portion of a catheter-based delivery system. The implantable pacemaker may be configured to be attached to a portion of a patient's heart, such as a ventricle.

Some embodiments disclose a medical device delivery assembly, the assembly comprising a catheter-based delivery system having an electrical pacing element at a tip region of the catheter-based delivery system. In some embodiments the delivery system is configured to receive a biocompatible material.

In some embodiments the biocompatible material comprises a prosthesis.

In some embodiments the prosthesis comprises a prosthetic heart valve. In some embodiments the pacing element comprises an implantable pacemaker.

In some embodiments the implantable pacemaker is configured to pace the heart during a procedure to implant the prosthetic heart valve. In some embodiments the implantable pacemaker is configured to contact a ventricle of the heart.

In some embodiments the implantable pacemaker is configured to pace the heart after a procedure to implant the prosthetic heart valve.

In some embodiments the electrical pacing element is configured to pace the heart during a heart valve repair procedure.

In some embodiments the catheter-based delivery system further comprises a lumen. In some embodiments the pacing element is configured to permit a delivery system element to pass thru the pacing element.

In some embodiments the pacing element comprises an electrode disposed proximate an end of the delivery system. In some embodiments the electrode is configured to receive and transmit electric current and contact the heart to provide pacing for at least a portion of time when the delivery system is present in the heart.

Some embodiments include a method for providing a medical device and pacing a heart, the method comprising introducing an assembly into a heart. In some embodiments the assembly comprises a delivery system having proximal and distal ends and includes an inner sheath and an outer sheath, a biocompatible material disposed on the inner sheath in a collapsed state and configured to expand to an expanded state. In some embodiments a pacing element can be positioned proximate a tip region of the delivery system.

In some embodiments the method comprises pacing the heart. In some embodiments the method may include retracting the outer sheath, implanting the biocompatible material, and removing the delivery system from the heart.

In some embodiments the biocompatible material comprises a prosthetic heart valve. In some embodiments pacing the heart comprises contacting a pacing element including an electrode to a wall of a ventricle before expanding the heart valve and providing electrical current to the electrode. In some embodiments pacing the heart ends prior to removing the delivery system from the heart.

In some embodiments the method comprises detaching the pacing element from the assembly and contacting the pacing element to a ventricle of the heart. In some embodiments pacing the heart occurs after removing the delivery system from the heart.

In some embodiments the prosthetic heart valve further comprises a valve assembly and a frame. In some embodiments pacing the heart comprises using the prosthetic heart valve with a conductive portion of the frame such that the conductive portion paces the heart.

In some embodiments the prosthetic heart valve further comprises a valve assembly and a frame. In some embodiments pacing the heart comprises using the prosthetic heart valve with conductive portions of the frame such that the conductive portions pace the heart.

In some embodiments the prosthetic heart valve further comprises an insulative portion of the frame.

In some embodiments pacing the heart further comprises contacting an implantable pacemaker to a ventricle and providing electrical current to the heart via the implantable pacemaker. In some embodiments pacing the heart continues after removing the delivery system from the heart.

In some embodiments the heart valve comprises a valve assembly, a frame, and a pacing strip.

In some embodiments the pacing strip comprises a conductive section attached to the frame of the heart valve to improve electrical communication in the heart.

In some embodiments the frame of the heart valve further comprises an insulated section to impede electrical communication in the heart.

In some embodiments the frame of the heart valve further comprises multiple insulated sections or multiple conductive sections.

In some embodiments an assembly for introduction into a heart is disclosed, the assembly comprising a delivery system having proximal and distal portions, a heart valve configured to collapse and expand, and an implantable pacemaker.

In some embodiments the delivery system comprises an inner sheath and an outer sheath. In some embodiments the inner sheath and outer sheath are configured to be retractable. In some embodiments wherein the heart valve is disposed on the inner sheath in a collapsed state. In some embodiments wherein the implantable pacemaker is disposed on the distal portion of the delivery system. In some embodiments the implantable pacemaker is configured to electrically pace the heart during and after implantation of the heart valve. In some embodiments the implantable pacemaker is configured to contact a ventricle of a heart and separate from the delivery system.

The embodiments and related concepts will be more fully understood from the following detailed description of the embodiments thereof.

DETAILED DESCRIPTION OF EMBODIMENTS

Figure 1A:
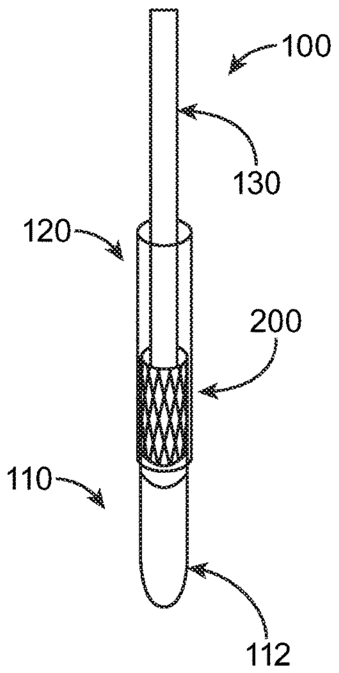
FIGS. 1A-1E illustrate a delivery system in accordance with some embodiments.

While the disclosure refers to illustrative embodiments for particular embodiments, it should be understood that the disclosure is not limited thereto. Modifications can be made to the embodiments described herein without departing from the spirit and scope of the present disclosure. Those skilled in the art with access to this disclosure will recognize additional modifications, embodiments, and embodiments within the scope of this disclosure and additional fields, in which the disclosed examples could be applied. Therefore, the following detailed description is not meant to be limiting. Further, it is understood that the apparatus and methods described below can be implemented in many different embodiments of hardware. Any actual hardware described is not meant to be limiting. The operation and behavior of the apparatus and methods presented are described with the understanding that modifications and variations of the embodiments are possible.

References to "one embodiment," "an embodiment," "some embodiments," "in certain embodiments," etc. . . . , indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An apparatus is disclosed to help with pacing of a patient's heart during or after a procedure on the patient. Incorporating a pacing element on to the delivery system simplifies the process of pacing the heart during a procedure and eliminates the need for a second procedure in some instances.

Sometimes while the physician performs a valve repair or prosthetic heart valve implantation, the physician may determine the need for addition pacing following the procedure. In some instances the physician may implant a pacing element during the same procedure rather than performing a second procedure to correct heart pacing problems. In other instances the physician may use a pacing element as a preventative measure. Using such a pacing element may be precautionary and prevent future heart pacing problems.

In some embodiments a delivery system is disclosed in which a TAVI is included as well as a pacing element. This pacing element may be incorporated directly onto a biocompatible material. Or this pacing element may be incorporated onto a secondary element disposed on a delivery system. This pacing element can help with pacing of a patient's heart before, during, and after a procedure. In some embodiments the pacing element may be an implantable pacing element.

In some embodiments the pacing element may be incorporated onto a biocompatible material itself. In some embodiments the biocompatible material may comprise a prosthesis or a prosthetic heart valve. In some embodiments a prosthetic heart valve may incorporate a highly conductive strip as part of the frame of the prosthetic heart valve frame.

This highly conductive strip or strips may facilitate communication near the atrioventricular (AV) node and may help the heart to function normally during or after implantation of a prosthetic heart valve. In some embodiments the conductive strip is configured to be positioned proximate a native heart valve. In some embodiments the conductive strip may be positioned proximate the sinoatrial node. The conductive strip may also facilitate communication near a different node or portion of a patient's heart. This strip may alternatively improve communication to any portion of the heart. This can prevent the need for a pacemaker to be implanted following the procedure with a biocompatible material or a prosthetic heart valve. In some embodiments the conductive strips may be comprised of a material with conductivity greater than nitinol or steel. One example may be silver or silver alloy. In some embodiments the conductive strips may be comprised of a biocompatible material. The conductive strip material may be configured such that the prosthetic heart valve may be configured to self-expand. The conductive strip material may be comprised of a material with sufficient elasticity to prevent chipping, cracking, or other problems when the material expands.

In some embodiments the conductive strips may create a new conductive pathway that may allow the AV node to function correctly after the prosthetic heart valve is implanted. This frame with conductive strips or portions may create a new conductive pathway for cardiac conductive signals or prevent the current conductive pathways from being affected by a biocompatible material, such a prosthetic heart valve. This may reduce the number of pacemaker implants required after treatment with a biocompatible material or prosthetic heart valve.

In some embodiments a portion of a prosthetic heart valve may include a coating. This coating may be a conductive coating or an insulative coating. This coating may be an alternative to a strip being attached to the frame of a prosthetic heart valve. In some embodiments the prosthetic heart valve may include both a conductive coating and an insulative coding. The insulative coating may prevent the prosthetic heart valve frame from interfering with the AV node's conductive pathway, and may it prevent the need to implant a pacemaker following deployment of a prosthetic heart valve. The disclosed apparatus may be used for pacing on either side of the heart. For example the apparatus may be used for pacing of the right atrioventricular valve or the left atrioventricular valve. It is contemplated that this apparatus can be used and adapted for multiple areas of the human heart, including multiple valve areas. In some embodiments the insulative strips may be comprised of a material with insulative properties greater than nitinol or steel. In some embodiments the insulative strips may be comprised of a biocompatible material. In some embodiments the insulative strips may be configured so that the prosthetic heart valve may be self-expanding. The insulative strip material may be comprised of a material with sufficient elasticity to prevent chipping, cracking, or other problems when the material expands.

Coating the frame with conductive or insulative coatings may prevent disturbance of the natural conductive pathways of the heart. Insulative coating of the frame may prevent radial conduction of the frame disposed inside the heart. This will prevent interruptions in the conductive pathways of the human heart.

In some embodiments the delivery system comprises a delivery assembly. The delivery assembly may comprise a catheter-based delivery system. This catheter-based delivery system may include an electrical pacing element. In some embodiments the electrical pacing element may be disposed at a tip region of the catheter-based delivery system. In some embodiments the delivery system is configured to receive a biocompatible material. This biocompatible material may be of many types. In some embodiments this biocompatible material may be a material used for heart valve repair on either side of a human heart. In some embodiments this biocompatible material may comprise a prosthesis or a device. In some embodiments this biocompatible material may comprise a prosthetic heart valve to be implanted in a patient. In some embodiments this biocompatible material may be another type of material to be received in a patient.

In some embodiments an electrical pacing element is included as an element of the delivery system. In some embodiments the pacing element comprises an implantable pacemaker. In some embodiments this implantable pacemaker is included as part of the delivery system in a combined fashion. In some embodiments the pacing element may include a portion of a biocompatible material and may be a prosthetic heart valve.

In some embodiments the pacing element may be an electrode disposed proximate the tip of the delivery system. This electrode may include a power source disposed on the delivery system or may include a power source separate from the delivery system. In some embodiments the pacing element is configured to pace the heart during or after a procedure on the patient's heart. This procedure may include a procedure to implant a prosthetic heart valve or valve repair.

In some embodiments an implantable pacemaker is configured to attach to a ventricle of the heart. In some embodiments the implantable pacemaker may be configured to be attached to a ventricle of the heart during the same procedure in which a prosthetic heart valve is implanted in the patient. In some embodiments the implantable pacemaker may be configured to be attached to a ventricle of the heart during the same procedure as a heart valve repair.

In some embodiments the implantable pacemaker is configured to pace the heart before, during, or after a procedure to implant a biocompatible material, such as a prosthetic heart valve. In some embodiments the implantable pacemaker is configured to pace the heart during and after a procedure on the heart. This procedure on the heart may include a valve repair procedure or a prosthetic heart valve implant procedure, among others.

In some embodiments the delivery system may comprise a guide lumen. This lumen may help to guide a guide wire or other elements of the delivery system. In some embodiments the pacing element or a portion of the pacing element may comprise a lumen. In some embodiments the implantable pacemaker may include a lumen.

In some embodiments the pacing element comprises an electrode. This electrode may be disposed at any point along or on any portion of the delivery system. In some embodiments the electrode may be disposed proximate the tip of the delivery system. In some embodiments this electrode may be disposed proximate the prosthetic heart valve disposed on the delivery system. In some embodiments this electrode may be configured to receive and transmit electric current. This electrode may also be configured to contact the heart and to provide pacing for some amount of time while the delivery system is present in the heart. In some embodiments this electrode may be configured to pace the heart after the delivery system has been removed from the heart.

Some embodiments disclose a method for providing a medical device and pacing a heart. This method may comprise introducing an assembly into a heart where the assembly may include a delivery system having a proximal and distal and. The assembly may also include an inner sheath and an outer sheath. The assembly may also include a biocompatible material disposed on some portion of the delivery system. In some embodiments this biocompatible material may be configured to collapse to a collapsed state and be configured to expand to an expanded state. The assembly may also comprise a pacing element on some portion of the delivery system. The pacing element may be positioned proximate a tip region of the delivery system.

The method may further include pacing the heart, retracting at least a portion of the delivery system, performing the procedure, and removing the delivery system from the heart.

In some embodiments the procedure performed with the disclosed assembly or apparatus may include a valve repair procedure or a prosthetic heart valve implant procedure or another procedure. In some embodiments this method may include pacing the heart by contacting a pacing element such as an electrode, to a wall of a heart ventricle. In some embodiments contacting the pacing element to the ventricle may occur before expanding a prosthesis, such as a prosthetic heart valve.

In some embodiments pacing the heart may begin or occur prior to removing the delivery system from the heart. The method may also comprise attaching the pacing element to a portion of the heart. And in some embodiments this detached pacing element may be configured to pace the heart after the delivery system is removed from the heart.

The pacing element may be disposed on part of a biocompatible material, such as a prosthesis. This prosthesis may be a prosthetic heart valve, such that the pacing element may be a strip of conductive material attached to a portion of the prosthetic heart valve. The conductive material may also be integrally incorporated into the frame of the prosthesis. In such embodiments, the frame is molded or otherwise made such that the conductive material is incorporated into the frame. In some embodiments the strip may be attached to the frame of the prosthetic heart valve. In some embodiments the prosthetic heart valve may include multiple strips. These multiple strips may include one or more conductive strips or one or more insulative strips or both. In some embodiments this conductive portion or portions of a prosthetic heart valve may pace the heart. This pacing may occur during a procedure or after the procedure has ended. In some embodiments the frame of the prosthetic heart valve comprises an insulated section or sections.

In some embodiments the prosthetic heart valve may comprise a coating rather than a strip. This coating may function similarly to a strip in that a conductive portion of prosthetic heart valve that is coated may improve pacing of a patient's heart.

The prosthetic heart valve may comprise a portion coated with an insulative coating. The insulative coating may prevent interruption of electrical communication within the heart.

In some embodiments the disclosed assembly is configured to be introduced into a heart. This assembly may comprise a delivery system having a proximal and distal portion, a prosthetic heart valve configured to collapse and expand, and an implantable pacemaker. The delivery system may also comprise an inner sheath and an outer sheath. In some embodiments one or both of these sheaths is configured to be retractable. In some embodiments a prosthesis, such as a prosthetic heart valve, is disposed on one of the sheaths in a collapsed state. In some embodiments the prosthesis is disposed in one of the sheaths.

In some embodiments an implantable pacemaker is disposed on a portion of the delivery system, such as the distal portion. In some embodiments an implantable pacemaker is configured to electrically pace the heart during and after a procedure on the heart. The implantable pacemaker may be configured to contact or be attached to a ventricle of the heart. This implantable pacemaker may also be separated from the delivery system via an actuator.

In some embodiments the pacing element is configured to contact a portion of the heart. In some embodiments the pacing element is configured to be joined to portion of the heart. In some embodiments the pacing element is configured to be attached to a portion of the heart.

FIG. 1A shows an assembly in accordance with some embodiments. In some embodiments the delivery system comprises catheter 100. In some embodiments catheter 100 may comprise tip 110, capsule 120, inner sheath 140, or outer sheath 130. In some embodiments catheter 100 may include a pacing element 112, a lumen 114, attachment projection 116, barb 118, springs 117, or pins 115.

In some embodiments tip 110 may be disposed at the end of catheter 100. In some embodiments tip 110 may be proximate capsule 120. In some embodiments capsule 120 may be proximate inner sheath 140 or outer sheath 130. In some embodiments one sheath may be proximate tip 110. In some embodiments tip 110 may taper from a larger cross-sectional area to a smaller cross-sectional area. The tip may be a pointed tip, a blunt tip, a cylindrical tip, or any other shape. In some embodiments the portion of the tip with a smaller cross-sectional area is disposed distal the end of the tip adjacent capsule 120.

In some embodiments tip 110 comprises a pacing element 112. In some embodiments pacing element 112 is contained within tip 110. In some embodiments pacing element 112 is disposed on tip 110. In some embodiments pacing element 112 may be proximate the narrowed portion of tip 110.

In some embodiments a biocompatible material 200 is disposed in a portion of catheter 100. In some embodiments a biocompatible material 200 is disposed on capsule 120 or another element of catheter 100. In some embodiments a biocompatible material 200 is disposed in capsule 120.

In some embodiments the biocompatible material 200 may comprise a prosthetic heart valve 300. The prosthetic heart valve 300 may comprise a valve assembly 310 and may comprise a frame 320. In some embodiments the frame 320 may comprise multiple portions. In some embodiments the frame 320 may comprise a conductive strip 322 or an insulative strip 324. The frame 320 may alternatively comprise a conductive coated portion 326 or an insulative coated portion 328. In some embodiments prosthetic heart valve 300 may also comprise a control arm 330 and at least one commissure post 340.

Figure 1B:
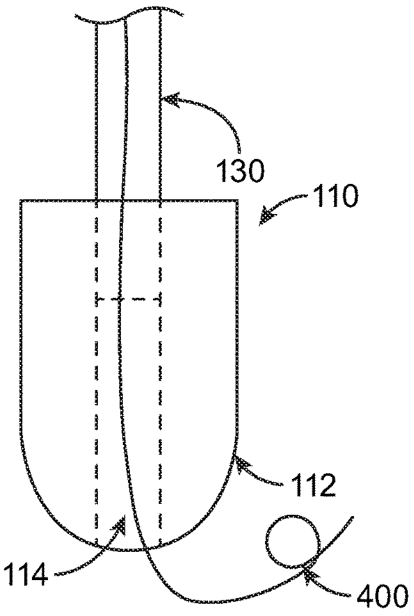

Referencing FIG. 1B, in some embodiments catheter 100 may comprise outer sheath 130, inner sheath 140, capsule 120, and tip 110. In some embodiments tip 110 may comprise a pacing element 112. In some embodiments tip 110 may also comprise a lumen 114. This lumen may be configured so that one or multiple elements of catheter 100 may pass through it. In some embodiments guide wire 400 may be able to pass through the lumen 114. In some embodiments lumen 114 is in the center of tip 110. In some embodiments lumen 114 is not in the center of tip 110.

In some embodiments lumen 114 is concentric with a sheath of catheter 100. This sheath may be either or both of inner sheath 140 or outer sheath 130. In some embodiments lumen 114 may be wider than a guide wire 400. In some embodiments tip 110 and the lumen 114 may be wider than a sheath of catheter 100. In some embodiments the tip 100 and the lumen 114 may be narrower than a sheath of catheter 100.

In some embodiments lumen 114 may tapered from a larger cross-sectional area to a smaller cross-sectional area. In some embodiments lumen 114 may run the entire length of tip 110. Alternatively, the lumen may run only a portion of the length of tip 110.

Figure 1C:
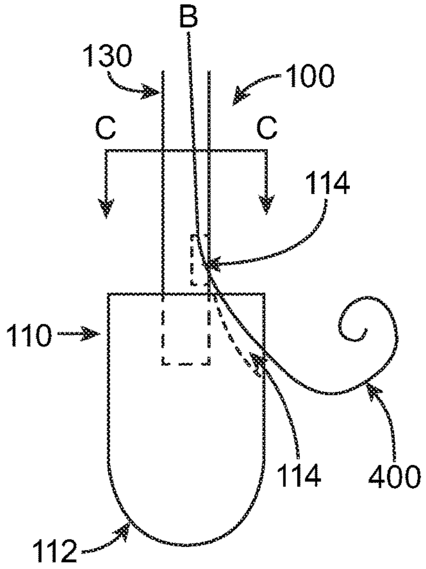

Now referring to FIG. 1C, in some embodiments the lumen 114 may not run through the center of tip 110. In some embodiments the lumen 114 may be disposed on a portion of tip 110. In some embodiments lumen 114 may be configured to receive a sheath of catheter 100. In some embodiments catheter 100 may include multiple lumens 114.

In some embodiments the multiple lumens are configured to receive a guide wire 400. In some embodiments the lumen 114 is configured to pass a guide wire 400 through a side of a sheath of catheter 100. In some embodiments the sheath may be outer sheath 130 or inner sheath 140. In some embodiments when guide wire 400 is fed through lumen 114, the guide wire 400 may pass through only a portion of the length of tip 100. In some embodiments pacing element 112 may comprise a lumen 114. In some embodiments the guide wire 400 is configured to be passed through at least a portion of pacing element 112 via a lumen 114.

Figure 1D:
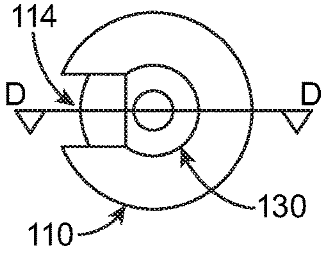
Figure 1E:
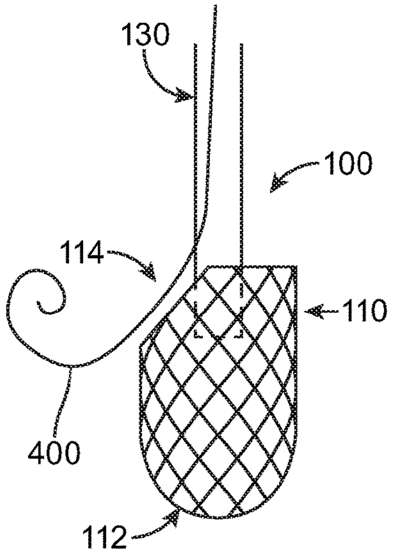

In some embodiments tip 110 comprises a recess or cut out. In some embodiments this cut out will comprises a hole or an aperture. In some embodiments this cut out will permit guide wire 400 to be fed out to the side of tip 110, as shown in FIG. 1D. In some embodiments this cut out or recess may be rectangular shaped, triangular shaped, or circular shaped. In some embodiments the lumen 114 passes through the side of a pacing element 112. In some embodiments the guide wire 400 is configured to be passed through one or both of tip 110 and pacing element 112. In some embodiments lumen 114 may create a sloped portion of tip 110 or pacing element 112, as shown in FIG. 1E. In some embodiments the lumen 114 may be symmetric. In some embodiments the lumen 114 may be asymmetric.

In some embodiments pacing element 112 may comprise an implantable pacemaker. Alternatively pacing element 112 may comprise an electrode. The pacing element may have a power source disposed on catheter 100 or may be connected to a power source not disposed on catheter 100. The power source may be outside the patient's heart 500.

In some embodiments pacing element 112 is configured to be detached from catheter 100. In some embodiments pacing element 112 is configured to be detached from tip 110. In some embodiments pacing element 112 may be configured to pace the patient's heart 500 during a procedure. This procedure may include a heart valve repair procedure, implanting a prosthetic heart valve, or another procedure on the heart.

Figure 2A:
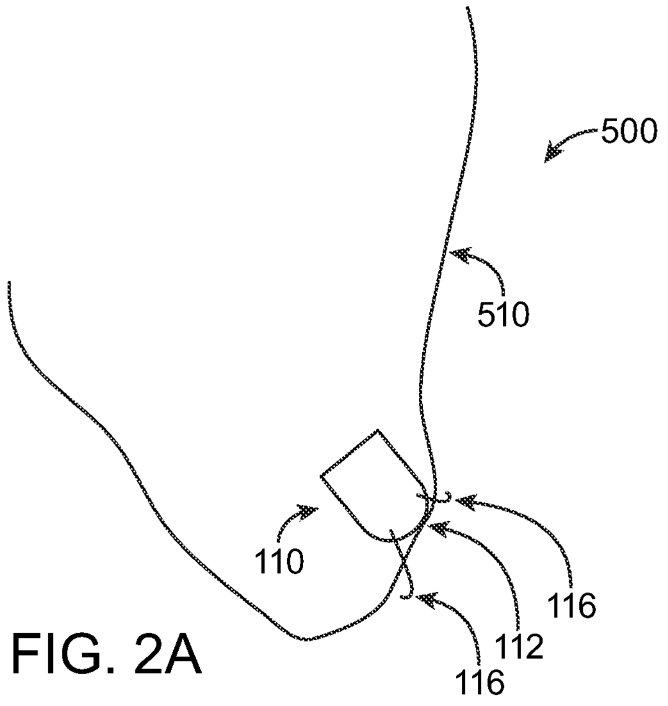
FIGS. 2A-2B illustrate a delivery system in accordance with some embodiments.

In some embodiments the pacing element is configured to contact a portion of the patient's heart 500. The pacing element may be configured to contact the ventricle 510, as shown in FIG. 2A. In some embodiments the pacing element 112 may be disposed at the narrowest point of tip 110. In some embodiments pacing element 112 may be disposed on tip 110. The pacing element 112 may be disposed in tip 110.

In some embodiments tip 110 may further comprise an attachment projection 116. Tip 110 may also comprise multiple attachment projections 116. In some embodiments these attachment projections 116 may be configured to deliver an electrical signal or stimulation to the patient's heart 500 or specifically the ventricle 510. In some embodiments the attachment projections are configured to couple the pacing element 112 with the ventricle 510. In some embodiments attachment projections 116 are configured to maintain contact of pacing element 112 with patient's heart 500.

In some embodiments attachment projections 116 may be substantially straight. In some embodiments pacing attachment projections 116 may be may comprise a straight and a curved portion. In some embodiments attachment projections 116 may be curved. Attachment projections 116 may be hook shaped.

In some embodiments pacing element 112 may comprise one, two, or more attachment projections 116. In some embodiments attachment projections 116 may extend away from tip 110. In some embodiments attachment ejections 116 may protrude from an end of tip 110. In some embodiments this will be a tapered or narrowed end of tip 110.

In some embodiments pacing element 112 may comprise an implantable pacemaker. This implantable pacemaker may comprise leads or it may be leadless. In some embodiments this implantable pacemaker may be small enough to be disposed on a catheter-based delivery system. In some embodiments this pacemaker may be disposed in a ventricle of a patient's heart. In some embodiments this pacemaker may be a percutaneous leadless pacing system.

Figure 2B:
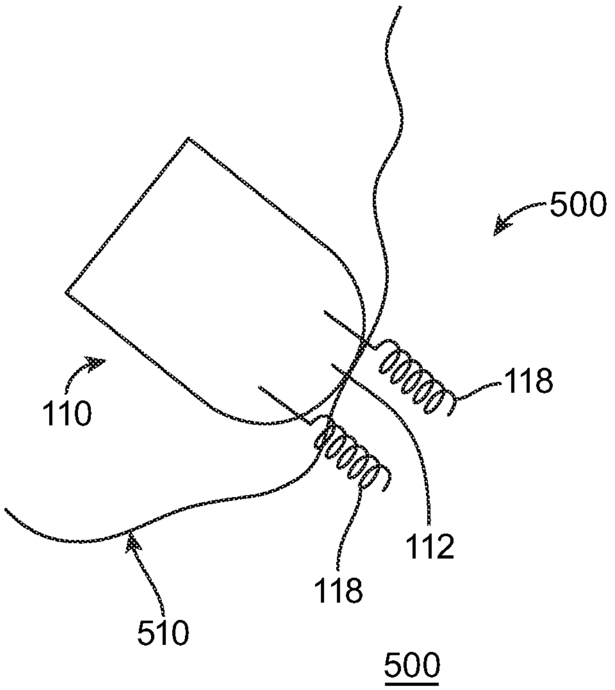

In some embodiments the pacing element 112 or tip 110 may contact the ventricle 510 through a barb 118, as shown in FIG. 2B. In some embodiments these barbs 118 may be threaded along a portion thereof. In some embodiments these barbs 118 may be coiled, wound, looped, twisted, or helical. In some embodiments these barbs 118 may be of varying lengths. In some embodiments each of barbs 118 may be similar or different in length. In some embodiments the diameter of the coils of each of the barbs 118 may be similar or different.

In some embodiments one barb 118 may include larger coils then another barb 118. In some embodiments the barbs 118 may comprise threads. In some embodiments barbs 118 may be configured to be advanced from tip 110 into ventricle 510. In some embodiments barbs 118 may be configured to contact a portion of a patient's heart 500. In some embodiments barbs 118 may comprise multiple coils. In some embodiments barbs 118 may comprise wire or other metal.

In some embodiments attachment projections 116 may comprise a metal, plastic, polymer, or a biocompatible material. In some embodiments attachment projections 116 may comprise a coating. In some embodiments this coating may help prevent interruption of electrical communication in patient's heart 500.

In some embodiments barbs 118 may extend more than half their length into the ventricle 510. In some embodiments barbs 118 may only extend a portion of their length into ventricle 510.

Figure 3A:
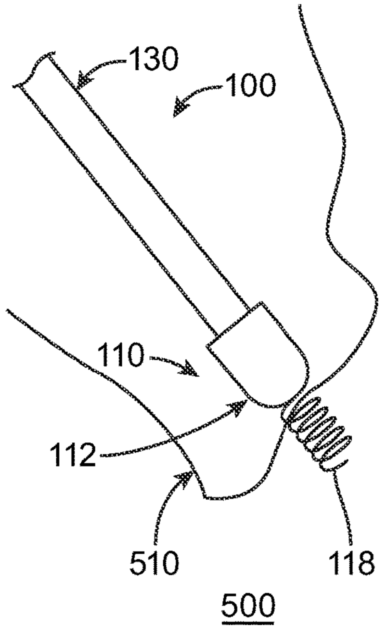
FIGS. 3A-3D illustrate a delivery system in accordance with some embodiments.

In referring to FIG. 3A, in some embodiments catheter 100 may comprise an outer sheath 130, an inner sheath 140, a capsule 120, and tip 110. In some embodiments tip 110 may comprise a pacing element 112. In some embodiments pacing element 112 may comprise a barb 118. In some embodiments barb 118 may extend from the center of tip 110 or pacing element 112. In some embodiments barb 118 may extend from a tapered portion of tip 110. In some embodiments tip 110 may be configured to be rotatable such that barb 118 may contact ventricle 510 of patient's heart 500. In some embodiments actuating tip 110 or pacing element 112 may result in barb 118 being advanced further into ventricle 510. Actuating barb 118 may also retract barb 118 from the ventricle 510. In some embodiments rotating tip 110 or pacing element 112 may result in barb 118 being advanced further into ventricle 510. Rotating barb 118 in a different direction may retract barb 118 from the ventricle 510.

In some embodiments barb 118 may comprise multiple coils or threads. In some embodiments barb 118 is configured to advance out of tip 110. This provides an advantage by being able to extend barb 118 when tip 110 is appropriately positioned. This also provides the advantage of preventing injury to a patient while the catheter 100 is being advanced to a deployment site.

Figure 3B:
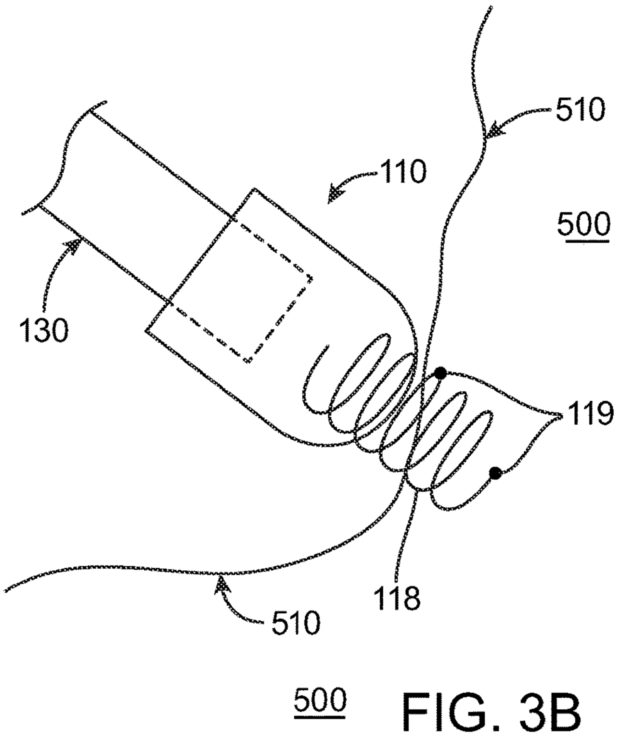

In referencing FIG. 3B catheter 100 may include outer sheath 130, capsule 120, and tip 110. In some embodiments tip 110 may comprise a barb 118 or an electrode 119. In some embodiments tip 110 may comprise multiple electrodes 119. These electrodes may be configured to deliver electrical signals to a portion of the patient's heart 500 or specifically to a ventricle 510. In some embodiments these electrodes may be configured to receive electrical signals from a power source disposed on catheter 100. In some embodiments these electrodes may be configured to receive electrical signals from a power source connected to catheter 100.

In some embodiments barb 118 may comprise an electrode 119 and barb 118 may be configured to be advanced from a portion of catheter of tip 110. In some embodiments pacing element 112 may comprise barb 118 or electrode 119. In some embodiments barb 118 can be threaded into ventricle 510 of patient's heart 500. In some embodiments a first electrode disposed on a barb 118 may be configured to provide a certain electrical signal or output while a second electrode 119 may be configured to provide a different electrical signal or output.

In some embodiments attachment projection 116, barb 118, or electrode 119 are configured to be advanced from tip 110 by actuating a separate portion of catheter 100. This actuation may come from a sheath 130 outer, inner sheath 140, or another element of catheter 100 such as a handle.

Figure 3C:
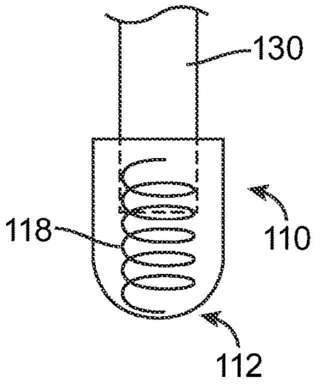

Referring to FIG. 3C, in some embodiments barb 118 may be configured to be contained within tip 110 temporarily. In some embodiments barb 118 may be configured to constrain a portion of catheter 100, such as outer shaft 130. In some embodiments barb 118 may be disposed around outer shaft 130. As shown in FIG. 3C, barb 118 may be configured to hold or constrain outer sheath 130 such that outer sheath 130 cannot move. Barb 118 may provide a mechanism to couple outer sheath 130 to tip 110.

Figure 3D:
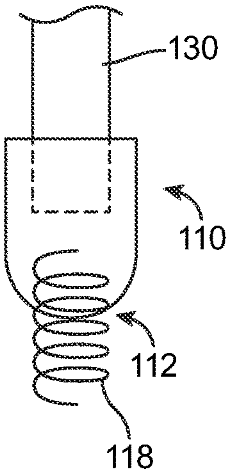

In some embodiments barb 118 is configured to be in an undeployed state and a deployed state. In some embodiments the undeployed state includes barb 118 being as least partially contained within this tip 110. In some embodiments barb 118 can be advanced out of tip 110 from the undeployed state to a deployed state. As shown in FIG. 3D, in the deployed state barb 118 may at least partially not be contained by tip 110.

In some embodiments the barb 118 is configured to be advanced via outer sheath 130, inner sheath 140, a handle of catheter 100, or capsule 120. In some embodiments barb 118 is advanced such that more than half of the length of barb 118 resides outside of tip 110. In some embodiments barb 118 is configured to be advanced from pacing element 112. In some embodiments barb 118 may comprise multiple coils.

In some embodiments some of the multiple coils of barb 118 may be configured to contact patient's heart 500, or more specifically a ventricle 510. In some embodiments after barb 118 is in a deployed state, a sheath of catheter 100 is less constrained. In some embodiments after barb 118 is in a deployed state the outer sheath 130 is configured to be separated from tip 110 or capsule 120. In some embodiments after barb 118 is advanced, capsule 120 is configured to be retracted or separated from tip 110.

Figure 4A:
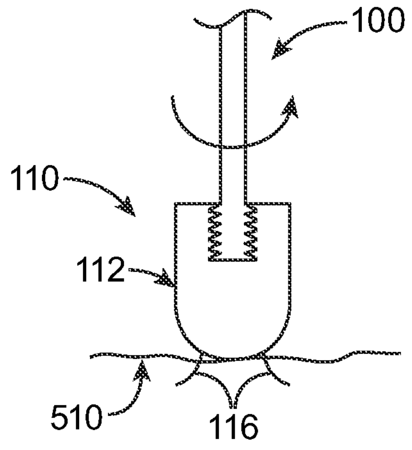
FIGS. 4A-4C illustrate a delivery system in accordance with some embodiments.
Figure 4B:
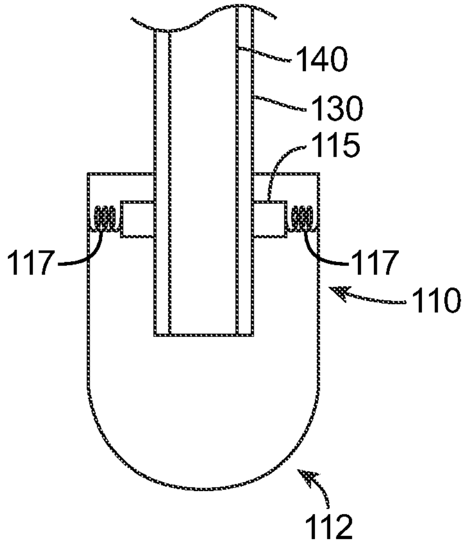
Figure 4C:
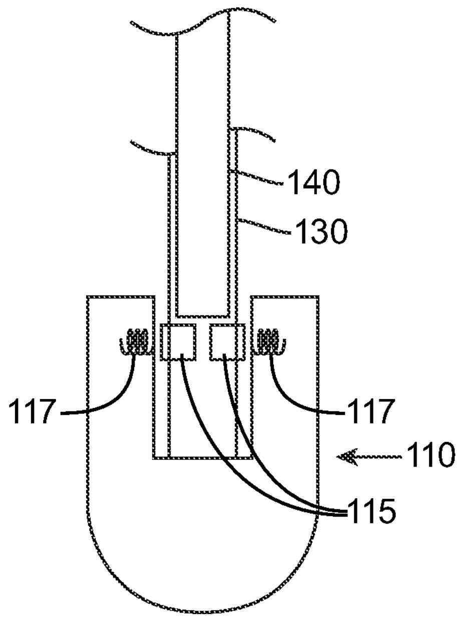

Referring to FIG. 4A, in some embodiments pacing element 112 is configured to be an implantable pacemaker. In some embodiments catheter 100 comprises a sheath, a tip 110, a pacing element 112, and attachment projections 116. As shown in FIG. 4A, catheter 100 may comprise a threaded sheath portion. In some embodiments tip 110 is configured to be advanced into a patient's heart 500 or ventricle 510. In some embodiments the tip 110 comprises attachment projections 116 or another attachment means. In some embodiments attachment projections 116 prevent tip 110 from separating from ventricle 510. In some embodiments when attachment projections 116 are in contact with patient's heart, attachment projections 116 prevent rotation of tip 110 or pacing element 112.

In some embodiments where catheter 100 comprises a threaded portion this threaded portion may be configured to be received by tip 110, as shown in FIG. 4A. In some embodiments the threaded portion of a sheath may be configured to be attached to tip 110 such that tip 110 is detachable from the threaded sheath of catheter 100. In some embodiments after attachment projections 116 are advanced into the patient's heart 500, the tip 110 is configured to be held in place and prevent rotation. In some embodiments after the pacing element 112 is positioned in the ventricle 510, the threaded sheath of catheter 100 may be rotated. This rotation may permit the threaded sheath to be removed or separated from the tip 110. Thus tip 110 may be attached or detachable from the rest of the catheter 100 system and may remain attached to the patient's heart 500. In some embodiments the multiple attachment projections 116 or other attachment means may provide the advantage of preventing rotation of the tip 110 while the sheath of catheter 100 is being rotated.

In some embodiments catheter 100 may comprise a tip 110, a capsule 120, an outer sheath 130, and an inner sheath 140. In some embodiments tip 110 may further comprise springs 117 distal from the tapered portion of tip 110. In some embodiments springs 117 may be disposed adjacent outer sheath 130. In some embodiments outer sheath 130 may comprise pins 115. In some embodiments pins 115 are configured to be positioned adjacent springs 117. In some embodiments pins 115 prevent tip 110 from detaching from outer sheath 130. In some embodiments springs 117 actuate pins 115. In some embodiments inner sheath 140 prevents springs 115 from being actuated by springs 117. In some embodiments the springs bias push pins 115 inward toward inner sheath 140 or outer sheath 130, which may be at least partially disposed within a portion of tip 110 or pacing element 112.

In some embodiments inner sheath 140 is configured to be retracted. When inner sheath 140 is retracted pins 115 are configured to be actuated by springs 117 such that tip 110 can be detached from or separated from a sheath of catheter 100 such as outer sheath 130. In some embodiments this detachment of tip 110 and a sheath of catheter 100 may occur after tip 110 or pacing element 112 is attached or contacted with a patient's heart 500. In some embodiments tip 110 may only comprise one pin 115 and one spring 117. In some embodiments outer sheath 130 may only comprise one pin 115 and one spring 117. In other embodiments tip 110 or outer sheath 130 may comprise multiple pins 115 or multiple springs 117.

In some embodiments an implantable pacemaker is configured to be disposed on a portion of catheter 100. In some embodiments pacing element 112 is configured to be an implantable pacemaker. This implantable pacemaker may be configured to be an appropriate size to be disposed on a catheter 100. This implantable pacemaker may be configured so that it can be delivered by a catheter 100 through a blood vessel.

In some embodiments this implantable pacemaker will be appropriately sized to fit the appropriate constraints of using a catheter-based delivery system. The implantable pacemaker may comprise a percutaneous leadless pacing system, a single chamber pacemaker, a dual chamber pacemaker, a biventricular pacemaker, or any other type. The implantable pacemaker may comprise zero, one, two, or more leads. The implantable pacemaker may comprise a power source or may be attached to a power source separate from the pacemaker.

Figure 5:
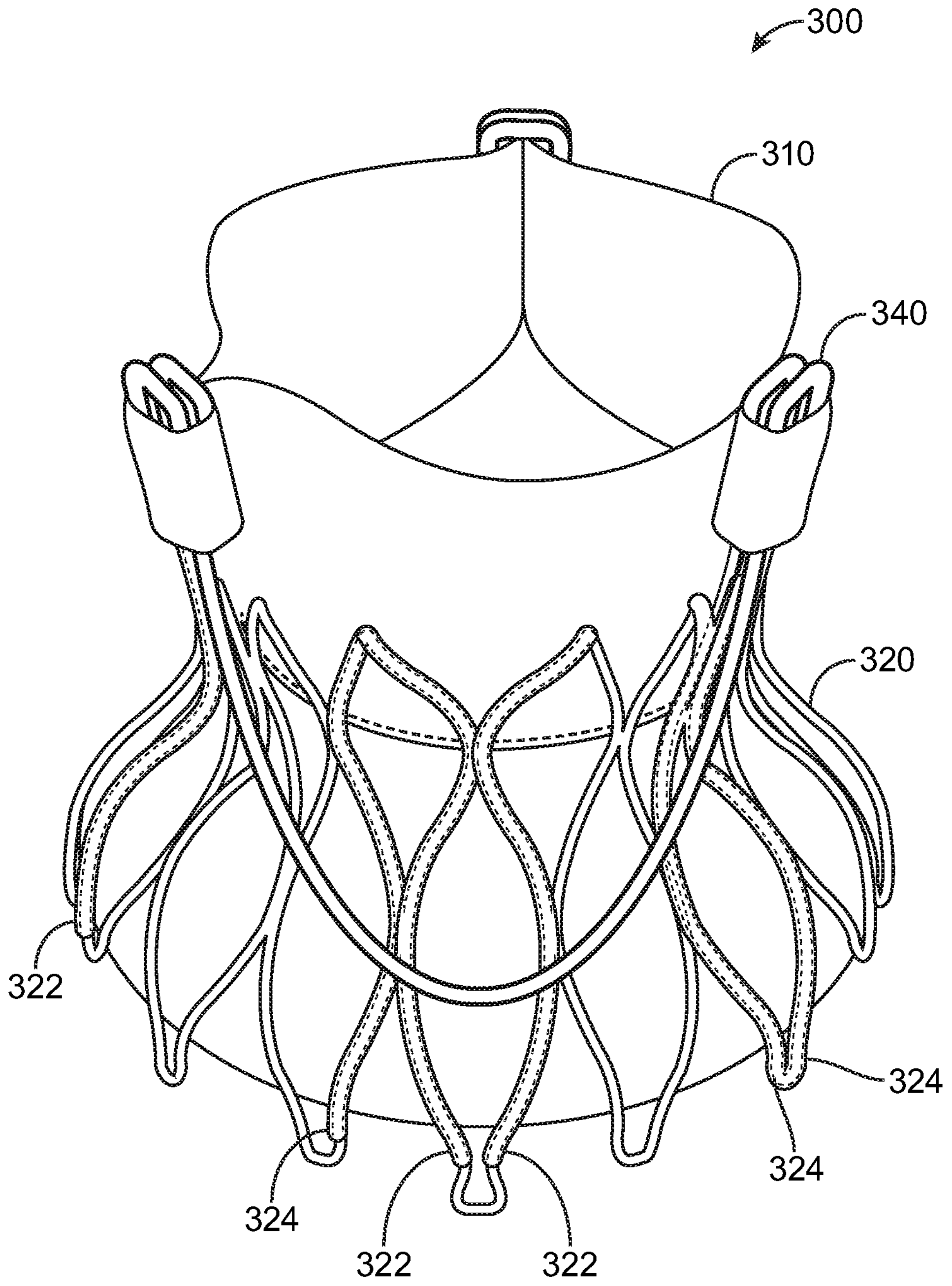
FIGS. 5-9 illustrate a prosthetic heart valve in accordance with some embodiments.

In accordance with some embodiments of the invention, as illustrated in FIG. 5, a pacing element 112 may be disposed on or be part of a prosthetic heart valve 300. In some embodiments the prosthetic heart valve 300 may comprise a valve assembly 310, a frame 320, a control arm 330, and at least one commissure post 340.

In some embodiments the valve assembly 310 may comprise multiple portions stitched or otherwise attached to each other. In some embodiments valve assembly 310 comprises bovine, porcine, biocompatible, or biological material. In some embodiments frame 320 comprises multiple elements. The frame 320 may constrain the valve assembly 310. In some embodiments the frame or a portion thereof may surround the valve assembly 310. In some embodiments the frame 320 or a portion thereof may be surrounded by valve assembly 310. In some embodiments frame 320 may further comprise attachment rings (not shown). In some embodiments frame 320 may be made of a biocompatible material, such as a wire.

In some embodiments frame 320 may interact with a patient's heart 500 such that the electrical communications of the patient's heart can be interrupted. In some embodiments frame 320 is configured to prevent, alleviate, or correct some of these problems.

As illustrated in FIG. 5, in some embodiments frame 320 comprises a conductive strip 322. The frame 320 may comprise petals, sections, division, segments, or portions. A segment of frame 320 may comprise a conductive strip 322. In some embodiments the conductive strip may extend from one end of one segment to the other end of the same segment. In some embodiments the conductive strip 322 surrounds a portion of the frame 322. In some embodiments the conductive strip extends from the end of the frame 320 distal the commissure post 340 to the other end of frame 320 proximate commissure post 340.

In some embodiments frame 320 may further comprise an insulative strip 324. This insulative strip 324 may help prevent interference by the frame 320 with the patient's heart 500 after a prosthetic heart valve 300 is placed in the patient. In some embodiments multiple portions of frame 320 may include insulative strips. Further, multiple portions of frame 320 may include conductive strips 322.

In some embodiments a conductive strip 322 may be may comprise one segment of frame 320 while and insulative strip 324 may comprise a second segment of frame 320. In some embodiments a conductive strip 322 may be positioned adjacent an insulative strip 324. In some embodiments frame 320 may comprise multiple conductive strips 322 and multiple insulative strips 324. In some embodiments the multiple conductive strips 322 and multiple insulative strips 324 may alternate or form a pattern. In some embodiments the insulative strips 324 may be configured to prevent the transmission of electrical energy to areas outside the target tissue or area. The insulative strips 324 may prevent unwanted interference with the electrical communication of the heart.

The conductive strips 322 can provide multiple benefits to the patient while the prosthetic heart valve 300 is present in the patient. The conductive strips 322 may correct pacing problems present before a prosthetic heart valve 300 was placed in the patient. The conductive strips 322 may correct pacing problems resulting from a prosthetic heart valve 300 being placed in the patient.

In some embodiments conductive strip 322 may create an additional pathway to facilitate electrical communication in a patient's heart 500, as illustrated in FIG. 5. Thus the conductive strips may prevent or correct pacing problems within the patient's heart. In some embodiments the conductive strips may comprise a portion of frame 320 that contacts a patient's heart 500. In some embodiments the conductive strips 322 are disposed on only a portion of a segment of frame 320.

Figure 6:
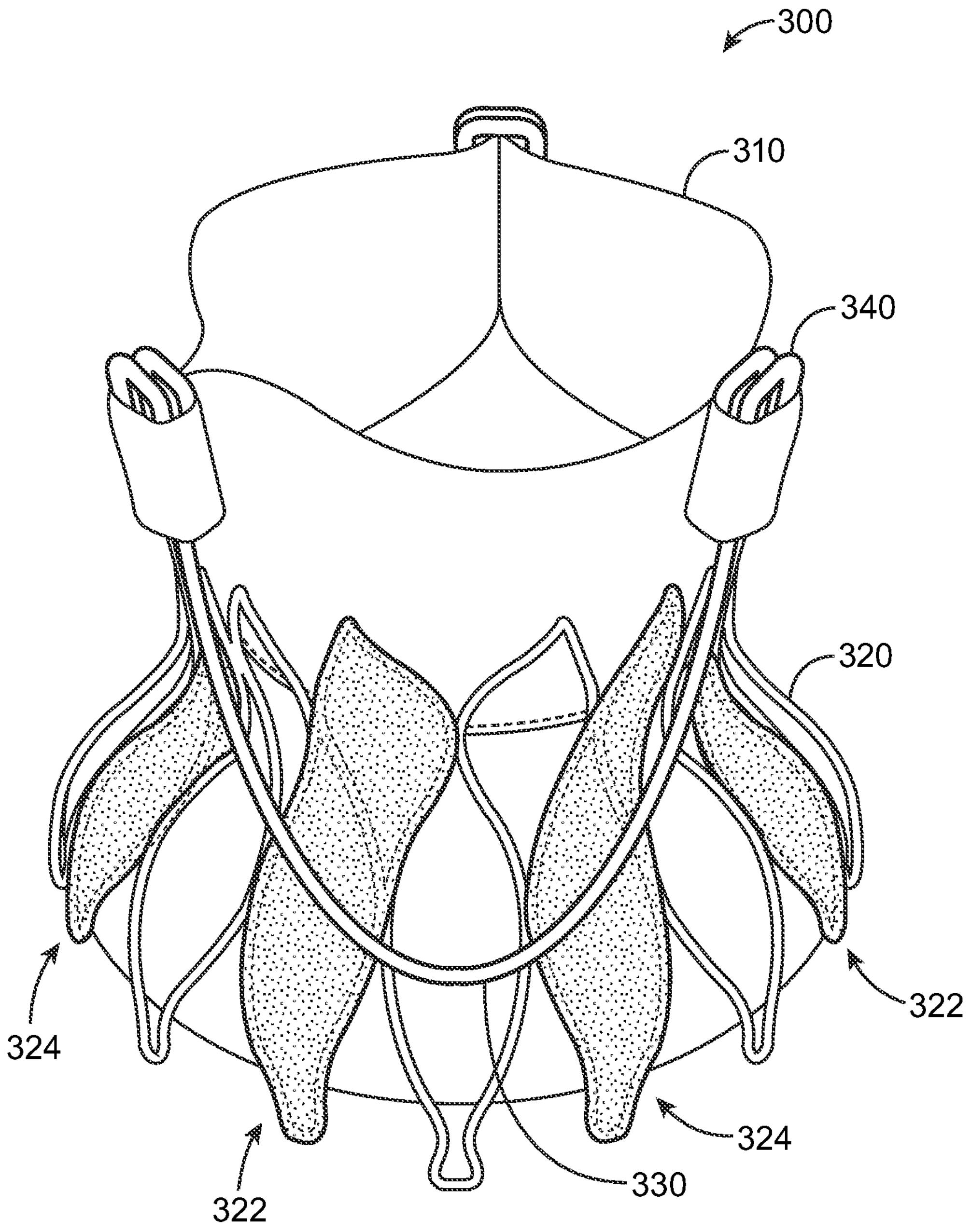

As shown in FIG. 6, conductive strips 322 may be disposed on portions of frame 320. In some embodiments conductive strips 322 cover more than one segment of frame 320. In some embodiments conductive strips 322 or insulative strips 324 may be asymmetric. In some embodiments conductive strips 322 may be a separate piece from frame 320.

In some embodiments conductive strip 322 extends and covers an opening between the wires of frame 320. In some embodiments conductive strips 322 are wider than the wires or elements that otherwise comprise frame 320, as shown in FIG. 6.

In some embodiments conductive strip 322 may taper to a point. In some embodiments the tapering of conductive strip 322 may follow the shape or outline of a segment or portion of frame 320. In some embodiments conductive strip 322 may extend from one end of a frame 322 to the other end of frame 322, as shown in FIG. 6.

In some embodiments conductive strips 322 may be vertical or horizontal. These conductive strips may be of various shapes. The shapes of conductive strips 322 may even vary on the same prosthetic heart valve 300. In some embodiments the conductive strips 322 may cover only a portion of frame 320. While in other cases the conductive strips 322 may cover multiple portions or every portion of frame 320.

In some embodiments conductive strips 322 comprise highly conductive materials. These conduct highly conductive materials may be any metal or other biocompatible material.

The same descriptions and characteristics described above regarding conductive strips 322 may also apply to the insulative strips 324. Similarly the same descriptions and characteristics described above regarding conductive strips 322 may also apply to the insulative strips 324.

In some embodiments the insulative strips 324 may alternate with the conductive strips 322. In some embodiments frame 320 may comprise an asymmetric conductive strip 322 as well as an asymmetric insulative strip 324. In some embodiments the total area of a conductive strip 322 may be more or less than the total area of an insulative strip 324. In some embodiments a conductive strip 322 may be configured to substantially contact a portion of a patient's heart 500, such as a native heart valve. In some embodiments conductive strips 322 may be configured to attach to a patient's heart 500. In some embodiments conductive strips 322 may be joined to portions of frame 320 by an adhesive, a clamp, welding, or any other means.

In some embodiments the conductive strips 322 may be integral with frame 320. In some embodiments the insulative strips 324 may be integral with frame 320. In some embodiments conductive strips 322 may be disposed on one side or area of frame 320, but not another side or area of frame 320. In some embodiments conductive strips 322 comprise multiple portions of frame 320.

Figure 7:
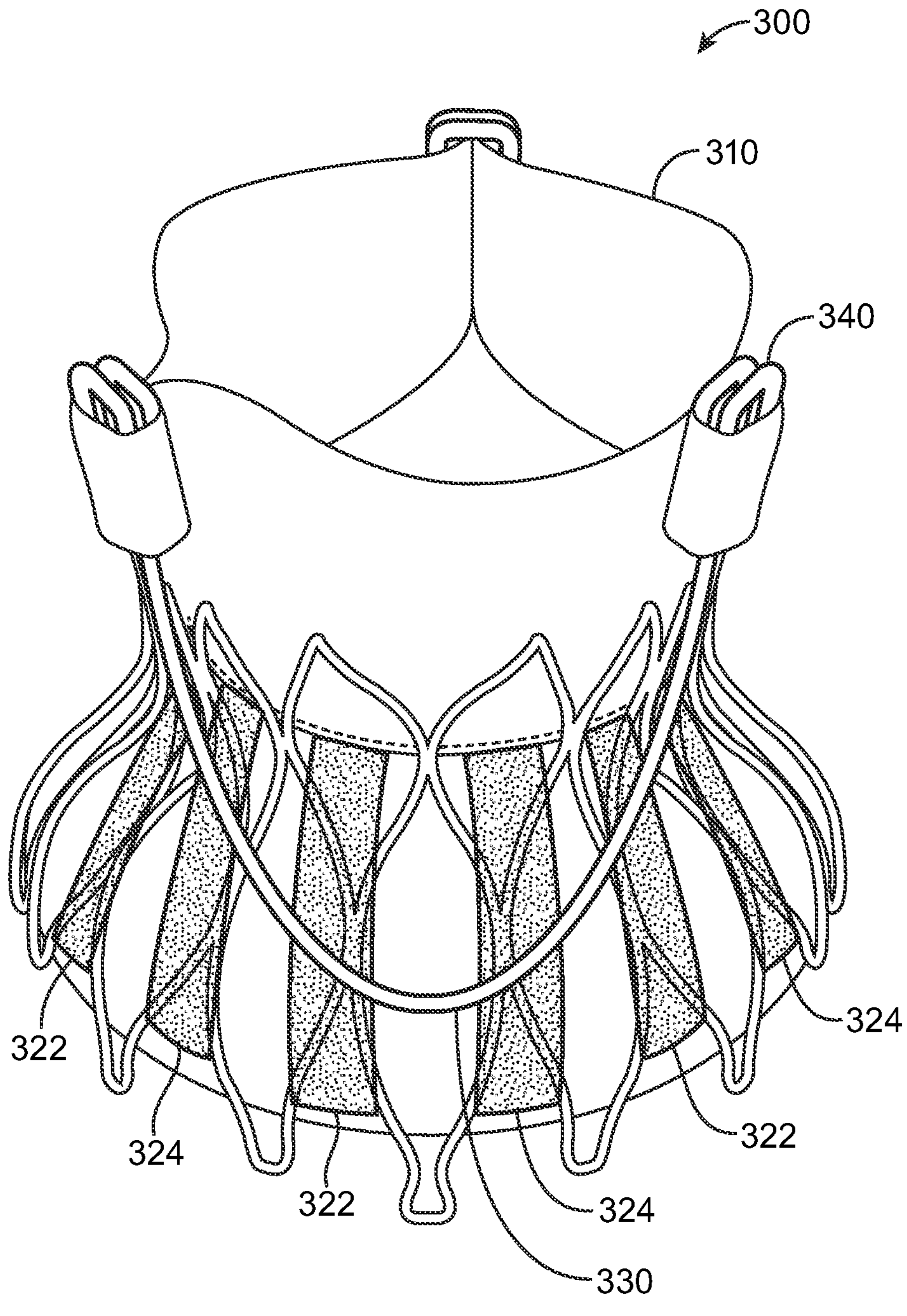

Referencing FIG. 7, in some embodiments conductive strips 322 or insulative strips 324 may be configured to be rectangular shaped. In some embodiments conductive strips 322 may be wider at the bottom than the top of the conductive strip. In some embodiments conductive strips 322 may be any geometric shape, such as a rectangle. In some embodiments conductive strips 322 may extend from one end of frame 320 toward another end of frame 320. In some embodiments conductive strips 322 may or may not extend the entire length of frame 320.

In some embodiments one conductive strip 322 may not directly contact or may not be adjacent to another conductive strip 322. In some embodiments a section of exposed frame 320 is adjacent to conductive strip 322 or insulative strip 324. In some embodiments conductive strip 322 may be oriented to run vertically as shown in FIG. 7. In some embodiments frame 320 has a distal and a proximal end, where the proximal end is proximate a commissure post 340. In some embodiments conductive strip 322 extends from the distal end of frame 320 toward the proximal end of frame 320.

In some embodiments conductive strip 322 has a constant width. In some embodiments conductive strip 322 has a varying width. In some embodiments conductive strip 322 is narrower than a segment of frame 320. In some embodiments conductive strip 322 is wider than a segment of frame 320. In some embodiments conductive strip 322 is wider than multiple segments of frame 320. In some embodiments conductive strip 322 is disposed on top of frame 322 such that conductive strip 322 may contact a patient's heart 500 when prosthetic heart valve 300 is placed in a patient.

Figure 8:
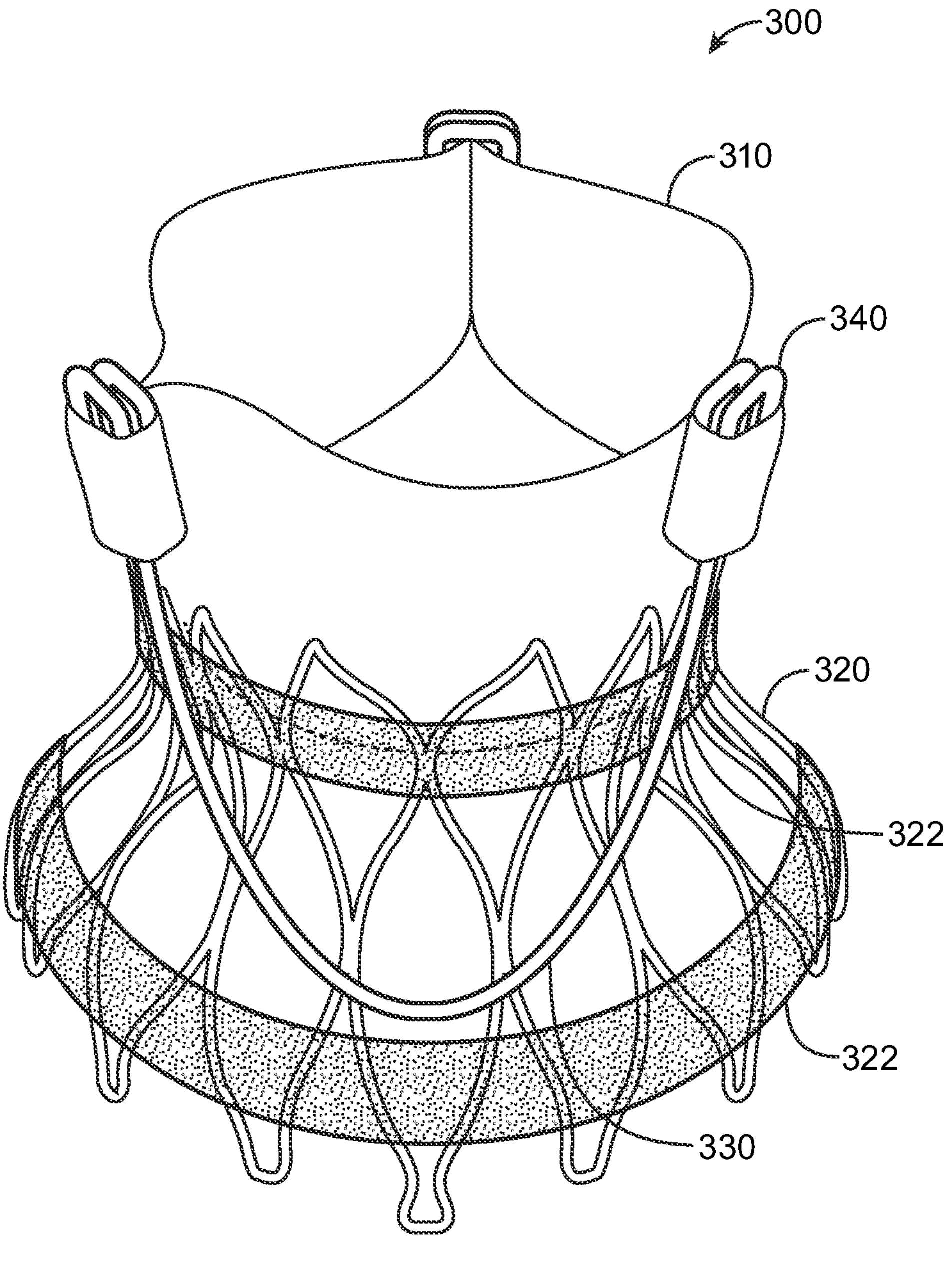

As shown in FIG. 8, in some embodiments conductive strips 322 may be disposed horizontally across frame 320. In some embodiments frame 320 may comprise multiple conductive strips oriented in a horizontal direction as shown in FIG. 8. In some embodiments the width of a conductive strip 322 may be less than or greater than the width of a segment of frame 320.

A conductive strip 322 may extend all the way around frame 320. In some embodiments conductive strip 322 may extend from the bottom or distal end of frame 320 to the end proximate a commissure. In this configuration with a single conductive strip 322 extending the full length of frame 320, the conductive strip 322 may resemble a skirt.

In some embodiments conductive strip 322 is joined only at certain points along its length to frame 320. In some embodiments conductive strip 322 is joined at every point along its length to frame 320.

In some embodiments an alternative to conductive strips 322 may be used with a prosthetic heart valve 300. In some embodiments a coating may be used. In some embodiments a conductive coating 326 may comprise a portion of frame 320. In some embodiments an insulative coating 328 may comprise a portion of frame 320. In some embodiments a conductive coating 326 or an insulative coating 328 may be applied to a segment of frame 320.

In some embodiments the portion of frame 320 comprising an conductive coating 326 may be asymmetric. In some embodiments the portion of frame 320 comprising an conductive coating 326 may be symmetric. In some embodiments the portion of frame 320 comprising an insulative coating 328 may be asymmetric. In some embodiments the portion of frame 320 comprising an insulative coating 328 may be symmetric.

In some embodiments a portion of frame 320 comprising a conductive coating 326 is adjacent to another portion of frame 320 comprising an insulative coating 328. Multiple portions of frame 320 may comprise a conductive coating 326. Similarly, multiple portions of frame 320 may comprise an insulative coating 328. In some embodiments frame 320 may comprise alternating conductive coating 326 portions and insulative coating 328 portions.

In some embodiments conductive coating 326 may be applied to the entire length of frame 320. In some embodiments conductive coating 326 may be applied only to a portion of the total length of frame 320.

Figure 9:
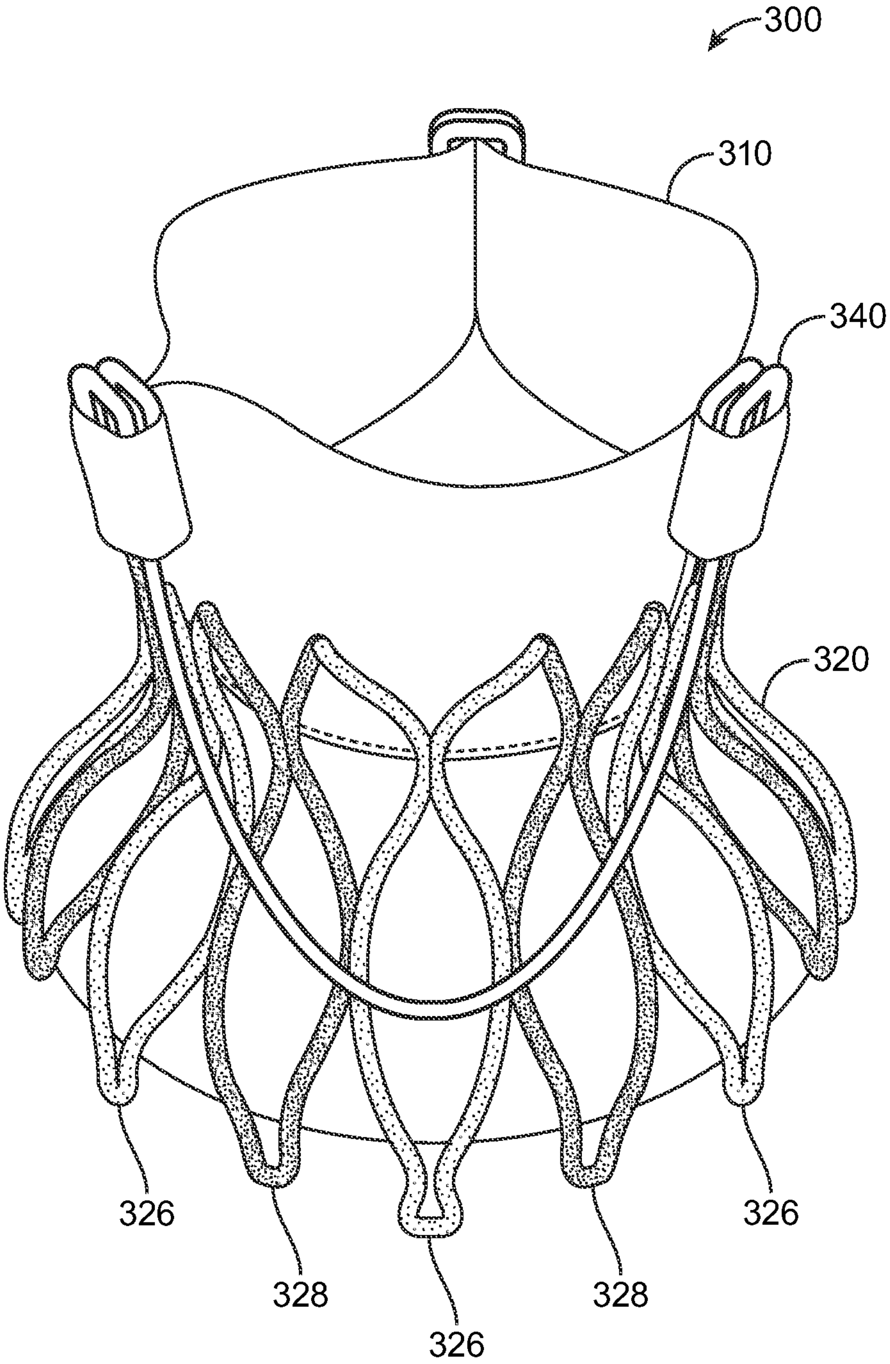

Referring now to FIG. 9, in some embodiments the surface area of frame 320 that comprises a conductive coating 326 may be the same surface area of frame 320 that comprises an insulative coating 328. In some embodiments the conductive coating 326 may be applied to at least a portion of frame 320 that contacts a patient's heart 500. In some embodiments the conductive coating 326 may be applied to the frame 320 after the valve assembly 310 and frame 320 are coupled together. In some embodiments the conductive coating 326 may be applied to the frame 320 before the valve assembly 310 and frame 320 are coupled together.

In some embodiments the conductive coating 326 helps prevent or correct abnormal electrical communication in a patient's heart 500. In some embodiments the conductive coating helps facilitate communication in the patient's heart 500.

The foregoing description has been presented for purposes of illustration and description. It is not intended to be exhaustive or to limit the precise embodiments disclosed. Any discussion related to one element disclosed may also apply with equal force to any other element. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A method of pacing a heart comprising:

delivering a catheter to a site of a native heart valve of the heart, the catheter including a distal tip and a capsule, the distal tip including a pacing element, wherein a prosthetic heart valve is disposed within the capsule, the prosthetic heart valve comprising a frame, a valve assembly, and a conductive strip coupled to the frame;

deploying the prosthetic heart valve from the capsule at the site of the native heart valve;

attaching the pacing element to a portion of the heart;

detaching the distal tip with the pacing element from the catheter; and pacing the heart.

2. The method of claim 1, wherein pacing the heart comprises pacing the heart during deployment of the prosthetic heart valve.

3. The method of claim 1, wherein the pacing the heart comprises pacing the heart after deployment of the prosthetic heart valve.

4. The method of claim 1, pacing the heart comprises pacing the heart via the pacing element prior to deployment of the prosthetic heart valve.

5. The method of claim 1, wherein the pacing element comprises a pacemaker.

6. The method of claim 1, wherein deploying the prosthetic heart valve comprises deploying the prosthetic heart valve such that the conductive strip is proximate the sinoatrial node of the heart.

* * * * *